United States Patent [19]

Zima et al.

[11] Patent Number: 5,393,905

[45] Date of Patent: Feb. 28, 1995

[54] PURIFICATION OF AMIDO-CARBOXYLIC ACIDS

[75] Inventors: George C. Zima, Kingsport; T. Hugh Williams, Fall Branch; Mark R. Shelton, Kingsport, all of Tenn.

[73] Assignee: Eastman Chemical Company, Kingsport, Tenn.

[21] Appl. No.: 228,612

[22] Filed: Apr. 15, 1994

[51] Int. Cl.⁶ .......................................... C07C 231/24
[52] U.S. Cl. ........................................ 554/70; 554/63; 554/68
[58] Field of Search ............................. 584/70, 63, 68

[56] References Cited

U.S. PATENT DOCUMENTS 2,453,234 11/1948 Keck .................................... 260/534
2,881,193 4/1959 Epstein et al. ........................ 554/63
2,956,068 10/1960 Dohr et al. ......................... 260/404.5

FOREIGN PATENT DOCUMENTS 648889 1/1951 United Kingdom .

*Primary Examiner*—José G. Dees
*Assistant Examiner*—Deborah D. Carr
*Attorney, Agent, or Firm*—John D. Thallemer

[57] ABSTRACT

This invention relates to a four step process for purifying amido-carboxylic acids by liquid/liquid extraction from a reaction mixture containing an amido-carboxylic acid. The first step involves distilling impurities from a reaction mixture containing an amido-carboxylic acid to form a distillate residue. The second step involves mixing the distillate residue with a nonpolar hydrocarbon solvent wherein the mixture is maintained above the freezing point of the distillate residue. The third step involves allowing the hydrocarbon solvent and distillate residue to achieve phase separation of an organic phase containing the amido-carboxylic acid and an organic phase containing the nonpolar hydrocarbon solvent. The fourth step involves separating the organic phase containing the nonpolar hydrocarbon solvent from the organic phase containing the amido-carboxylic acid.

7 Claims, No Drawings

PURIFICATION OF AMIDO-CARBOXYLIC ACIDS

FIELD OF INVENTION

This invention relates to a four step process for purifying amido-carboxylic acids by liquid/liquid extraction from a reaction mixture containing an amido-carboxylic acid. The first step involves distilling impurities from a reaction mixture containing an amido-carboxylic acid to form a distillate residue. The second step involves mixing the distillate residue with a nonpolar hydrocarbon solvent wherein the mixture is maintained above the freezing point of the distillate residue. The third step involves allowing the hydrocarbon solvent and distillate residue to achieve phase separation of an organic phase containing the amido-carboxylic acid and an organic phase containing the nonpolar hydrocarbon solvent. The fourth step involves separating the organic phase containing the nonpolar hydrocarbon solvent from the organic phase containing the amido-carboxylic acid.

BACKGROUND OF THE INVENTION

Amido-carboxylic acids are industrial chemical intermediates for the preparation of many chemicals used in commerce. For example, amido-carboxylic acids are used to make bleach activators for detergents. Amido-carboxylic acids are generally prepared by reacting a lactam or an amino acid with a carboxylic acid.

U.S. Pat. No. 2,453,234 discloses a process for preparing an amino-carboxylic acid by hydrolyzing a lactam by means of at least 10 moles of water per mole of lactam to produce an amino-carboxylic acid. Great Britain Pat. No. 648,889 discloses a process for preparing amino-carboxylic acids by heating aliphatic or cycloaliphatic lactams in the presence of more than 20 moles of water per mole of lactam. U.S. Pat. No. 2,956,068 discloses a process for preparing amido-carboxylic acids by reacting a lactam with a free carboxylic acid in the presence of catalytic amounts of water. The reaction product is obtained as a solid crystal mass which is subsequently suspended in water and neutralized.

Amido-carboxylic acids prepared by processes as mentioned above are purified either by crystallization or by solvent leaching. In solvent leaching, the solid amido-carboxylic acids are suspended in an organic solvent, filtered and washed. The slurry/wash procedure is repeated. The disadvantage of these purification processes are that low yields of the amido-carboxylic acid product is obtained.

In contrast, the present inventors have unexpectedly discovered a liquid/liquid extraction process for purifying amido-carboxylic acids which generates a high yield of the amido-carboxylic acid.

SUMMARY OF THE INVENTION

Accordingly, it is one object of the present invention to provide a process for purifying amido-carboxylic acids from a reaction mixture containing an amido-carboxylic acid.

Accordingly, it is another object of the invention to provide a liquid/liquid extraction process for purifying amido-carboxylic acids which generates a high yield of the purified amido-carboxylic acid.

These and other objects are accomplished herein by a process for purifying amido-carboxylic acids by liquid/liquid extraction from a reaction mixture containing an amido-carboxylic acid, said process comprising the steps of:

(A) distilling impurities from a reaction mixture containing an amido-carboxylic acid under reduced pressure to form a distillate residue;

(B) mixing the distillate residue from Step (A) with a nonpolar hydrocarbon solvent having 5 to 30 carbon atoms wherein the amount of the nonpolar hydrocarbon solvent is 0.1 to 10 times the weight of the distillate residue and the mixture of the hydrocarbon solvent and the distillate residue is maintained above the freezing point of the distillate residue;

(C) allowing the hydrocarbon solvent and distillate residue to achieve phase separation of an organic phase containing the amido-carboxylic acid and an organic phase containing the nonpolar hydrocarbon solvent; and (D) decanting the organic phase containing the nonpolar hydrocarbon solvent from the organic phase containing the amido-carboxylic acid.

DESCRIPTION OF THE INVENTION

The process of the present invention for purifying amido-carboxylic acids by liquid/liquid extraction from a reaction mixture generally containing water, lactams, amino acids, carboxylic acids or esters and amido-carboxylic acids involves four steps. The first step involves distilling impurities and unreacted starting materials such as lactams and carboxylic acids from the reaction mixture under reduced pressure to form a distillate residue.

The distillation is generally conducted at a temperature of 80° C. to 250° C. under vacuum, preferably 120° C. to 220° C. It is important to note, however, that at the higher temperatures in this range, the amido-carboxylic acid product may polymerize to form oligomers or cyclize to form a lactam. Therefore, care must be taken to limit the distillation time when higher temperatures are employed. The distillation time can be very short, for example, flash distillation of less than 5 minutes. It is preferable to use lower temperatures in the temperature range with a vacuum of less than 3 mm Hg. For example, octanoic and decanoic acid can be removed at a temperature of 120° C. if the vacuum is less than 3 mm Hg.

The second step, Step (B), involves adding a nonpolar hydrocarbon solvent to the distillate residue from Step (A) and applying agitation to mix the nonpolar hydrocarbon solvent and the distillate residue. The mixture of the nonpolar hydrocarbon solvent and the distillate residue must be maintained above the freezing point of the distillate residue. In other words, the distillate residue needs to be a fluid and should not contain solid particles which may interfere with phase separation in Step (C) below. The freezing point of the distillate residue depends on the amount of carboxylic acid present in the residue. Generally the freezing point of the distillate residue is approximately 50° to 80° C. A temperature above the freezing point of the distillate residue is accomplished by heating the nonpolar hydrocarbon solvent prior to addition with the distillate residue, and/or by maintaining the distillate residue at a temperature above its freezing point.

The nonpolar hydrocarbon solvent may be a cyclic or acyclic aliphatic hydrocarbon solvent or an aromatic hydrocarbon solvent as long as the amido-carboxylic acid is essentially insoluble in the nonpolar hydrocarbon solvent. The term "essentially insoluble" means that the amido-carboxylic acid either has limited solubility in the nonpolar hydrocarbon solvent or is insoluble. The nonpolar hydrocarbon solvent has 5 to 30 carbon atoms, preferably 5 to 20 carbon atoms, and most preferably 6 to 10 carbon atoms. Examples of nonpolar hydrocarbon solvents include: heptane, hexane, octane, dodecane, cyclohexane, cyclooctane, benzene, toluene, xylene, and cumene.

The choice of nonpolar hydrocarbon solvent depends on the impurities such as carboxylic acids which are removed from the reaction mixture containing an amido-carboxylic acid. It is recommended but not necessary for the practice of the process of this invention that in the case where short chain carboxylic acids having 6 to 10 carbon atoms are used, short chain nonpolar hydrocarbon solvents having 5 to 15 carbon atoms are preferred. Likewise, in the case where long chain carboxylic acids having 11 to 26 carbon atoms are used, longer chain nonpolar hydrocarbon solvents are preferred.

The nonpolar hydrocarbon solvent is present in an amount of 0.1 to 10 times the weight of the distillate residue, preferably 1 to 5 times. Most preferably, the nonpolar hydrocarbon solvent is present in an amount of 1 to 2 times the weight of the distillate residue. Insufficient nonpolar hydrocarbon solvent results in unsatisfactory separation between the phases. Although there is no critical higher limit to the amount of nonpolar hydrocarbon solvent, the use of greater than 10 times the weight of the distillate residue creates a situation where it is increasingly difficult to separate the distillation residue phase containing the amido-carboxylic acid from the much larger nonpolar hydrocarbon solvent phase which would render the process unnecessarily expensive from the point of view of recovering the desired product in pure form.

The third step, Step (C), involves ceasing agitation and allowing the hydrocarbon solvent and distillate residue to achieve phase separation. The organic phase containing the amido-carboxylic acid separates from the organic phase containing the nonpolar hydrocarbon solvent. The two organic phases must be immiscible or no separation will occur.

The fourth step, Step (D), involves separating the organic phase containing the nonpolar hydrocarbon solvent from the organic phase containing the amido-carboxylic acid product. Separation is accomplished by methods known in the art such as decantation. Steps (B), (C) and (D) may be repeated wherein the distillate residue is replaced with the organic phase containing the amido-carboxylic acid to further purify the amido-carboxylic acid. Generally five extractions will yield greater than 90% of amido-carboxylic acid product. Steps (B), (C) and (D) may be repeated until amido-carboxylic acid of a desired purity is obtained.

The process of the present invention for purifying amido-carboxylic acids by liquid/liquid extraction may be conducted stepwise as a batch process or as a continuous process.

The process of the present invention will be further illustrated by a consideration of the following examples, which are intended to be exemplary of the invention.

EXAMPLE 1

A crude molten 6-(N-decamido) caproic acid reaction mixture after distillation, 89 grams, was combined with an equal weight of heptane. The resulting mixture was heated to reflux (approx. 98° C.) for two minutes. Agitation was stopped which achieved phase separation of an organic phase containing the amido-carboxylic acid and an organic phase containing the heptane. The phases were separated by decantation. The organic phase containing the amido-carboxylic acid product was extracted four additional times with equal weights of heptane.

Each organic phase containing the heptane extracts were evaporated to dryness on a rotary evaporator. Analytical data for the organic phase containing the amido-carboxylic acid product is summarized in Table I. It is important to note that the last column in Table I titled "Vac. Dried" refers to the fifth extraction sample which was dried under vacuum. 81.4 grams of amidocaproic acid was recovered from 89.0 grams of distillation residue after five heptane extractions which is a 91% yield.

Analytical data for the organic phase containing the heptane is summarized in Table II. 5.3 grams total residue from extracts equaled 6.0% yield based on initial charge. 81.4 grams of amidocaproic acid and 5.3 grams of residue was recovered from 89.0 grams of distillation residue. Therefore, 97.4% of the distillation residue was accounted for after five heptane extractions and evaporation of the solvent.

TABLE I

| | Organic Phase Containing the Amido-Carboxylic Acid | | | | | | |
|---|---|---|---|---|---|---|---|
| Extract No. | Starting Material | 1 | 2 | 3 | 4 | 5 | Vac. Dried |
| % Caprolactam | <0.1 | 0.4 | 0.6 | <0.1 | <0.1 | 0.6 | 0.4 |
| % Decanoic Acid | 8.9 | 6.4 | 5.8 | 5.4 | 4.3 | 4.1 | 4.2 |
| % Unknown | | 1.9 | 0.7 | <0.1 | <0.1 | <0.1 | <0.1 |
| % Acylcaprolactam | 4.3 | 1.6 | 1.2 | <0.1 | 1.0 | 1.0 | 1.2 |
| % Unknown | | 1.2 | 1.2 | 1.2 | 1.2 | 1.0 | 1.2 |
| % Amido Caproic Acid | 72.5 | 73.0 | 76.0 | 80.3 | 80.6 | 80.1 | 82.3 |
| % C-10 Diamidocaproic acid | 14.3 | 14.6 | 12.2 | 14.2 | 12.3 | 12.4 | 7.6 |

The results in Table I clearly show that the process of the present invention for purifying amido-carboxylic acids by liquid/liquid extraction from a reaction mixture leads to an amidocaproic acid product with lower levels of impurities as compared to the crude distillate. In addition, Table I indicates that the amount of impurities such as acylcaprolactam and decanoic acid decreased with each extraction step.

TABLE II

| Organic Phase Containing the Hydrocarbon Solvent | | | | | |
|---|---|---|---|---|---|
| Extract No. | 1 | 2 | 3 | 4 | 5 |
| Grams Residue | 1.79 | 1.35 | 0.82 | 0.65 | 0.69 |
| % Caprolactam | 1.0 | 4.7 | 7.0 | 3.1 | 1.2 |

TABLE II-continued

| Organic Phase Containing the Hydrocarbon Solvent | | | | | |
|---|---|---|---|---|---|
| Extract No. | 1 | 2 | 3 | 4 | 5 |
| % Decanoic Acid | 34.1 | 38.7 | 42.0 | 41.8 | 39.4 |
| % Unknown | 6.3 | 7.0 | 7.2 | 7.2 | 7.2 |
| % Unknown | 9.4 | 9.9 | 9.9 | 9.7 | 9.4 |
| % Acylcaprolactam | 29.8 | 19.7 | 15.8 | 10.8 | 8.7 |
| % Unknown | 7.4 | 4.1 | 2.1 | 2.8 | 1.7 |
| % Amidocaproic acid | 12.9 | 13.7 | 14.0 | 21.8 | 29.1 |
| % C-10 Diamido caproic acid | 1.1 | 1.9 | 1.6 | 2.5 | 3.0 |

Table II lists the impurities which are removed with each extraction step.

Many variations will suggest themselves to those skilled in this art in light of the above detailed description. All such obvious modifications are within the full intended scope of the appended claims.

What is claimed is:

1. A process for purifying amido-carboxylic acids by liquid/liquid extraction from a reaction mixture containing an amido-carboxylic acid, said process comprising the steps of:
   (A) distilling impurities at a temperature of 80° C. to 250° C. under vacuum from a reaction mixture containing an amido-carboxylic acid under reduced pressure to form a distillate residue;
   (B) mixing the distillate residue from Step (A) with a nonpolar hydrocarbon solvent having 5 to 30 carbon atoms wherein the amount of the nonpolar hydrocarbon solvent is 0.1 to 10 times the weight of the distillate residue and the mixture of the hydrocarbon solvent and the distillate residue is maintained above the freezing point of the distillate residue;
   (C) allowing the hydrocarbon solvent and distillate residue to achieve phase separation of an organic phase containing the amido-carboxylic acid and an organic phase containing the nonpolar hydrocarbon solvent; and
   (D) separating the organic phase containing the nonpolar hydrocarbon solvent from the organic phase containing the amido-carboxylic acid.

2. The process of claim 1 wherein the nonpolar hydrocarbon solvent is selected from the group consisting of cyclic nonpolar hydrocarbon solvents, acyclic nonpolar hydrocarbon solvents, aromatic nonpolar hydrocarbon solvents, and combinations thereof.

3. The process of claim 2 wherein the nonpolar hydrocarbon solvent is selected from the group consisting of heptane, hexane, octane, dodecane, cyclohexane, cyclooctane, benzene, toluene, xylene, and cumene.

4. The process of claim 1 wherein the nonpolar hydrocarbon solvent has 5 to 20 carbon atoms.

5. The process of claim 4 wherein the nonpolar hydrocarbon solvent has 6 to 10 carbon atoms.

6. A process for purifying amido-carboxylic acids by liquid/liquid extraction from a reaction mixture containing an amido-carboxylic acid, said process comprising the steps of:
   (A) distilling impurities at a temperature of 120° C. to 220° C. under vacuum from a reaction mixture containing an amido-carboxylic acid under reduced pressure to form a distillate residue;
   (B) mixing the distillate residue from Step (A) with a nonpolar hydrocarbon solvent having 5 to 30 carbon atoms wherein the amount of the nonpolar hydrocarbon solvent is 1 to 5 times the weight of the distillate residue and the mixture of the hydrocarbon solvent and the distillate residue is maintained above the freezing point of the distillate residue;
   (C) allowing the hydrocarbon solvent and distillate residue to achieve phase separation of an organic phase containing the amido-carboxylic acid and an organic phase containing the nonpolar hydrocarbon solvent;
   (D) decanting the organic phase containing the nonpolar hydrocarbon solvent from the organic phase containing the amido-carboxylic acid; and
   (E) repeating Steps (B), (C) and (D) wherein the distillate residue is replaced with the organic phase containing the amido-carboxylic acid.

7. The process of claim 6 wherein the nonpolar hydrocarbon solvent is present in an amount of 1 to 2 times the weight of the distillate residue.

* * * * *